(12) United States Patent
Callahan et al.

(10) Patent No.: US 12,021,377 B2
(45) Date of Patent: Jun. 25, 2024

(54) POWER MANAGEMENT SYSTEM

(71) Applicant: THE BOEING COMPANY, Chicago, IL (US)

(72) Inventors: Kevin S. Callahan, Everett, WA (US); Teresa King, Chicago, IL (US)

(73) Assignee: THE BOEING COMPANY, Chicago, IL (US)

( * ) Notice: Subject to any disclaimer, the term of this patent is extended or adjusted under 35 U.S.C. 154(b) by 413 days.

(21) Appl. No.: 17/352,819

(22) Filed: Jun. 21, 2021

(65) Prior Publication Data
US 2021/0394924 A1 Dec. 23, 2021

Related U.S. Application Data

(60) Provisional application No. 63/042,626, filed on Jun. 23, 2020.

(51) Int. Cl.
*H02J 1/14* (2006.01)
*A61L 2/10* (2006.01)

(52) U.S. Cl.
CPC ............... *H02J 1/14* (2013.01); *A61L 2/10* (2013.01); *A61L 2202/14* (2013.01); *A61L 2202/25* (2013.01); *H02J 2310/44* (2020.01)

(58) Field of Classification Search
CPC .... A61L 2/10; A61L 2202/14; A61L 2202/25; H02J 1/14; H02J 2310/44
USPC ........................................................ 323/234
See application file for complete search history.

(56) References Cited

U.S. PATENT DOCUMENTS

| | | | | |
|---|---|---|---|---|
| 9,327,600 | B1* | 5/2016 | Nehmeh | B60L 1/00 |
| 9,579,255 | B2 | 2/2017 | Arxium | |
| 2006/0042846 | A1* | 3/2006 | Kojori | G05B 9/03 |
| | | | | 180/65.8 |
| 2015/0102662 | A1* | 4/2015 | Walstrom | B60R 16/03 |
| | | | | 307/9.1 |
| 2015/0159552 | A1* | 6/2015 | Rodriguez | F02C 7/32 |
| | | | | 290/2 |
| 2019/0225323 | A1* | 7/2019 | Rhoden | F02C 9/28 |
| 2019/0366872 | A1 | 12/2019 | Kanamori et al. | |

FOREIGN PATENT DOCUMENTS

EP 2579412 A1 4/2013

OTHER PUBLICATIONS

European Search Report for related European Patent Application No. EP 21 18 1121 dated Dec. 7, 2021 (7 pages).

* cited by examiner

*Primary Examiner* — Yemane Mehari
(74) *Attorney, Agent, or Firm* — Joseph M. Butscher; THE SMALL PATENT LAW GROUP LLC

(57) ABSTRACT

A power management system has a controller including one or more processors. The controller is configured to monitor electrical power on a power bus of a vehicle. The power bus is electrically connecting a power source to multiple subsystems of the vehicle for powering the subsystems via the electrical power on the power bus. The controller is further configured to determine that the electrical power on the power bus exceeds a designated power generation limit, and, in response, generate a reduction command message for communication to a lowest-priority subsystem of the subsystems. The reduction command message instructs the lowest-priority subsystem to reduce power consumption.

20 Claims, 12 Drawing Sheets

POWER MANAGEMENT SYSTEM

CROSS-REFERENCE TO RELATED APPLICATIONS

This application relates to and claims priority benefits from U.S. Provisional Patent Application No. 63/042,626, filed 23 Jun. 2020 and entitled "Power Management System," which is hereby incorporated by reference in its entirety.

FIELD OF THE DISCLOSURE

Embodiments of the present disclosure generally relate to systems and methods that manage the electrical power generated by a power source onboard a vehicle and utilized by one or more subsystems of the vehicle.

BACKGROUND OF THE DISCLOSURE

Vehicles such as commercial aircraft have onboard generators that power various subsystems onboard the vehicles, such as propulsion systems, environmental control systems, equipment and instrument systems, lighting systems, appliances, electronics and display systems, and the like. When the power generation reaches a limit due to the various loads concurrently drawing power, typical electrical load management systems compensate by temporarily deactivating or disconnecting one or more entire subsystems from the power bus. For example, if an oven in a galley is operating at a time at which the power generation limit is exceeded, the load management system may alleviate the excess load by shutting off the oven as well as other appliances in the galley. The binary response of shedding entire subsystems when the power generation limit is reached causes a complete disruption of the functions of those particular subsystems.

SUMMARY OF THE DISCLOSURE

A need exists for a system and a method for eliminating the "all or nothing" binary approach for electrical load management in vehicles, such as commercial aircraft.

With those needs in mind, certain embodiments of the present disclosure provide a power management system that has a controller including one or more processors. The controller is configured to monitor electrical power on a power bus of a vehicle. The power bus is electrically connecting a power source to multiple subsystems of the vehicle for powering the subsystems via the electrical power on the power bus. The controller is further configured to determine that the electrical power on the power bus exceeds a designated power generation limit, and, in response, generate a reduction command message for communication to a lowest-priority subsystem of the subsystems. The reduction command message instructs the lowest-priority subsystem to reduce power consumption.

In one or more embodiments, a method for allocating power amount vehicle subsystems provided. The method includes monitoring, via a controller including one or more processors, electrical power on a power bus of a vehicle. The power bus electrically connects a power source to multiple subsystems of the vehicle for powering the subsystems via the electrical power on the power bus. Responsive to determining that the electrical power on the power bus exceeds a designated power generation limit, the method includes generating a reduction command message for communication to a lowest-priority subsystem of the subsystems. The reduction command message instructs the lowest-priority subsystem to reduce power consumption.

In one or more embodiments, a power management system is provided that includes a controller and a sanitizing system. The controller includes one or more processors and is configured to monitor electrical power on a power bus of a vehicle. The power bus electrically connects a power source to multiple subsystems of the vehicle for powering the subsystems via the electrical power on the power bus. The sanitizing system represents one of the subsystems. The sanitizing system includes a plurality of ultraviolet (UV) lamps mounted at various locations within an internal cabin of the vehicle and configured to emit UV light into the internal cabin using the electrical power on the power bus. The controller is further configured to determine that the electrical power on the power bus exceeds a designated power generation limit, and, in response, generate a reduction command message for communication to the sanitizing system. The reduction command message instructs the sanitizing system to reduce power consumption. The sanitizing system is configured to reduce an amount of power supplied to one or more of the UV lamps, based on the reduction command message, to diminish the UV light output from the one or more UV lamps without causing the one or more UV lamps to cease emitting UV light.

DETAILED DESCRIPTION OF THE DISCLOSURE

Figure 1:
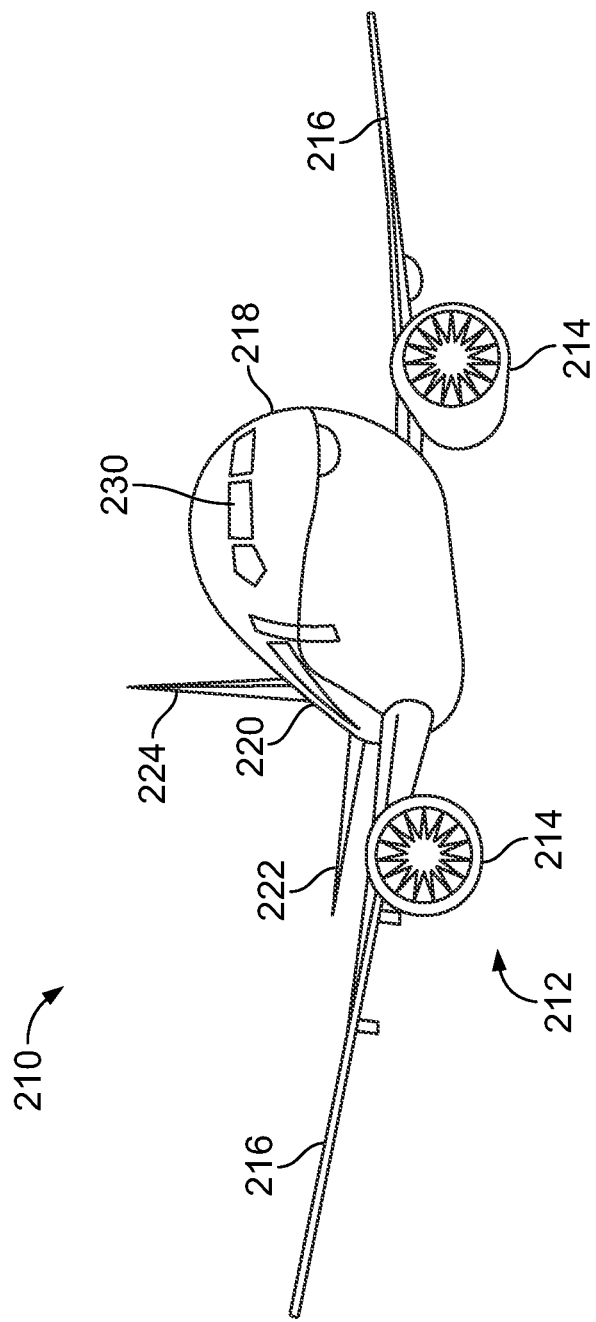
FIG. 1 illustrates a perspective front view of an aircraft, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a power management system for vehicles, such as commercial aircraft. The power management system equitably allocates power between multiple member systems (referred to herein as subsystems) that draw electrical power from a shared power bus. An onboard power source (or power generation system) supplies the electrical power to the power bus. The power management system disclosed herein controls one or more of the subsystems to operate a reduced power levels as needed to maintain compliance with a designated power generation limit. The power generation limit represents a designated upper threshold of electrical power on the power bus. The power management system manages the subsystems to maintain the power generation limit by taking action when the total power draw or demand exceeds or approaches the power generation limit. For example, if the power draw exceeds the power generation limit, the power management system instructs one or more of the subsystems to reduce power (without necessarily disconnecting or deactivating the subsystems) until the power deficit is remedied. In an embodiment, only subsystems classified as non-essential to the operation of the vehicle and health and wellness of the vehicle occupants are considered for a power reduction. The power management system arranges the non-essential subsystems in order of priority, and the lowest-priority subsystem is the first to receive an instruction to reduce power, followed by the second lowest-priority subsystem if necessary, and the like. When there is sufficient power capacity available, all subsystems operate normally. When that limit is exceeded (perhaps from a galley oven turning on), then the subsystem with the lowest priority decreases its power first. Furthermore, as described herein, the individual subsystems may have their own priority arrangements, such that the lowest-priority subsystem first reduces power from one or more lowest-priority electrical devices than and then reduces power from higher-priority electrical devices in the subsystem as needed to satisfy the deficit.

In addition to equitably controlling power allocation amongst subsystems, the power management system also provides a proportional response to surpassing the power generation limit. For example, the power management system determines the deficit in the power budget, meaning the amount of power that needs to be reduced in order to comply with the power generation limit. Rather than merely deactivating an entire low-priority subsystem, the power management system communicates the deficit to one or more of the subsystems, including at least the lowest-priority subsystem. If the lowest-priority subsystem draws more power than the deficit, then the lowest-priority subsystem reduces its power consumption by the deficit amount. The lowest-priority subsystem only needs to reduce its power consumption by the deficit amount, and can continue to consume power from the power bus after making the power reduction. For example, if the lowest-priority subsystem draws 10 kW of power and receives an instruction that the deficit is 6 kW, then the lowest-priority subsystem reduces its power consumption to 4 kW to satisfy the budget deficit. The lowest-priority subsystem can continue to operate at 4 kW until further notice such that the subsystem can continue to function, just at a reduced power level. As such, the power management system proportionally responds to deficits in the power budget, without binarily shutting off subsystems to reduce the load, which avoids complete disruption of subsystem functionality. For example, subsystems and their devices may be configured to continue operating and functioning, although the operations may take longer to complete, provide diminished or degraded output, or the like due to the decreased power supply. The power management system described herein is adaptable to allow a non-essential system to utilize all available electrical power by adapting its consumption in synchronization with the onboard power source (e.g., power generation system).

In one or more embodiments, one of the member systems or subsystems of the vehicle managed by the power management system is a sanitizing system. The sanitizing system includes a plurality of ultraviolet (UV) light sources (referred to herein as UV lamps) arranged within an internal cabin of the vehicle. The UV lamps are positioned and controlled to emit UV light into the internal cabin during travel of the vehicle such that the UV light sanitizes air and surfaces within the internal cabin. The emitted UV light may be controlled to exhibit a designated wavelength or narrow wavelength range that is safe for human tissue. For example, the designated wavelength may be 222 nm. The UV lamps are positioned to sanitize air and surfaces before the air and surfaces can be cleaned via air filtering (e.g., with HEPA filters) in the air movement and conditioning system or manual application of chemical cleaners within the vehicle, such as may occur between trips. At least some of the UV lamps may be operated to persistently emit UV light for extended periods of time. For example, at least some of the UV lamps may be on (e.g., active) to continuously emit UV light throughout an entire duration of a trip, from the time that passengers board the vehicle to the time that passengers deboard. The persistent UV emission kills or neutralizes pathogens to prohibit the spread of pathogens in the air and on surfaces during travel of the vehicle, between cabin cleanings and air conditioning cycles.

The sanitizing system may be classified as the lowest-priority non-essential subsystem or one of the lower-priority non-essential subsystems. As a result, in one or more embodiments, the power management system may request that the sanitizing system decrease power draw to remedy a determined deficit in the power budget. The sanitizing system can proportionally decrease its power draw by reducing the power supplied to one or more of the UV lamps, such as one or more subsets of UV lamps in low-priority areas of the internal cabin, as described herein. The sanitizing system can operate the one or more subsets of UV lamps at lower power levels to satisfy the power reduction request while at least some of the UV lamps in the one or more subsets continue to emit UV light. For example, the UV lamps that receive less power may merely emit UV light with less intensity and/or range than prior to the power reduction request, such that are least some of the UV lamps may continue to function to sanitize and disinfect the internal cabin.

FIG. 1 illustrates a perspective front view of an aircraft 10, according to an embodiment of the present disclosure. The aircraft 10 includes a propulsion system 12 that includes engines 14, for example. Optionally, the propulsion system 12 may include more engines 14 than shown. The engines 14 are carried by wings 16 of the aircraft 10. In other embodiments, the engines 14 may be carried by a fuselage 18 and/or an empennage 20. The empennage 20 may also support horizontal stabilizers 22 and a vertical stabilizer 24.

The fuselage 18 of the aircraft 10 defines an internal cabin, which includes a flight deck or cockpit, one or more work sections (for example, galleys, personnel carry-on baggage areas, and the like), one or more passenger sections (for example, first class, business class, and coach sections), one or more lavatories, and/or the like.

Alternatively, instead of an aircraft, embodiments of the present disclosure may be used with various other vehicles, such as automobiles, buses, rail vehicles, watercraft, and the like. For example, the power management system disclosed herein can be implemented on a passenger train, a bus, a passenger boat, and the like. Embodiments of the present disclosure may also be used with respect to enclosed areas within fixed structures, such as commercial and residential buildings. Some of the fixed structures may have independent power generation systems, such that the fixed structures do not use power from a grid, similar to vehicles. Other fixed structures can utilize power from a grid, but still implement the power management system as disclosed herein to maintain a designated power generation limit for limiting energy usage and costs. For example, the power management system and sanitizing system can be installed and operated within theatres, concert venues, places of worship, office buildings, stores, and the like, where persistent UV light at non-harmful wavelengths can provide continuous disinfection of air and surfaces.

Figure 2A:
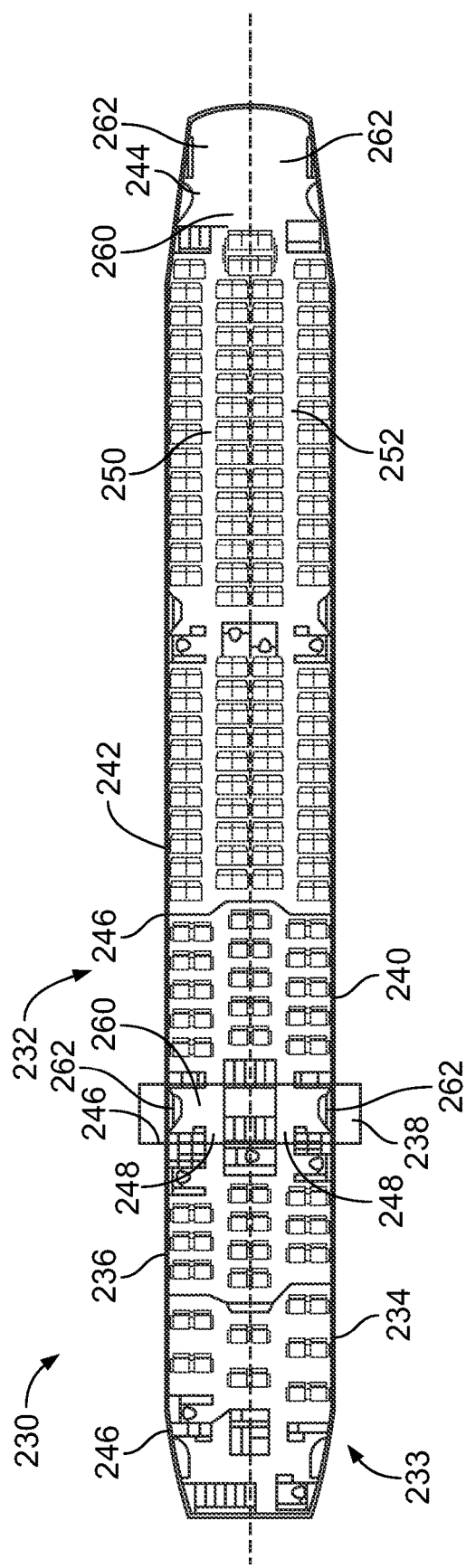
FIG. 2A illustrates a top plan view of an internal cabin of an aircraft, according to an embodiment of the present disclosure.

FIG. 2A illustrates a top plan view of an internal cabin 30 of an aircraft, according to an embodiment of the present disclosure. The internal cabin 30 may be within the fuselage 18 of the aircraft 10 shown in FIG. 1. For example, one or more fuselage walls may define the internal cabin 30. The internal cabin 30 includes multiple sections, including a front section 33, a first-class section 34, a business class section 36, a front galley station 38, an expanded economy or coach section 40, a standard economy of coach section 42, and an aft section 44. The internal cabin 30 also includes multiple lavatories 45. It is to be understood that the internal cabin 30 may include more or less sections than shown. For example, the internal cabin 30 may not include a first-class section, and may include more or less galley stations than shown. Each of the sections may be separated by a cabin transition area 46, which may include class divider assemblies 48.

As shown in FIG. 2A, the internal cabin 30 includes two aisles 50 and 52 that extend a substantial length of the internal cabin 30 and lead to the aft section 44. The aisles 50 and 52 extend to egress paths or door passageways 60. Exit doors 62 are located at ends of the egress paths 60. The egress paths 60 may be perpendicular to the aisles 250 and 252. The internal cabin 30 may include more egress paths 60 at different locations than shown. Optionally, the internal cabin 30 may have less or more aisles than shown. For example, the internal cabin 30 may include a single aisle that extends through the center of the internal cabin 30 that leads to the aft section 44. The sanitizing system described herein may be used to sanitize air and various structures within the internal cabin 30.

Figure 2B:
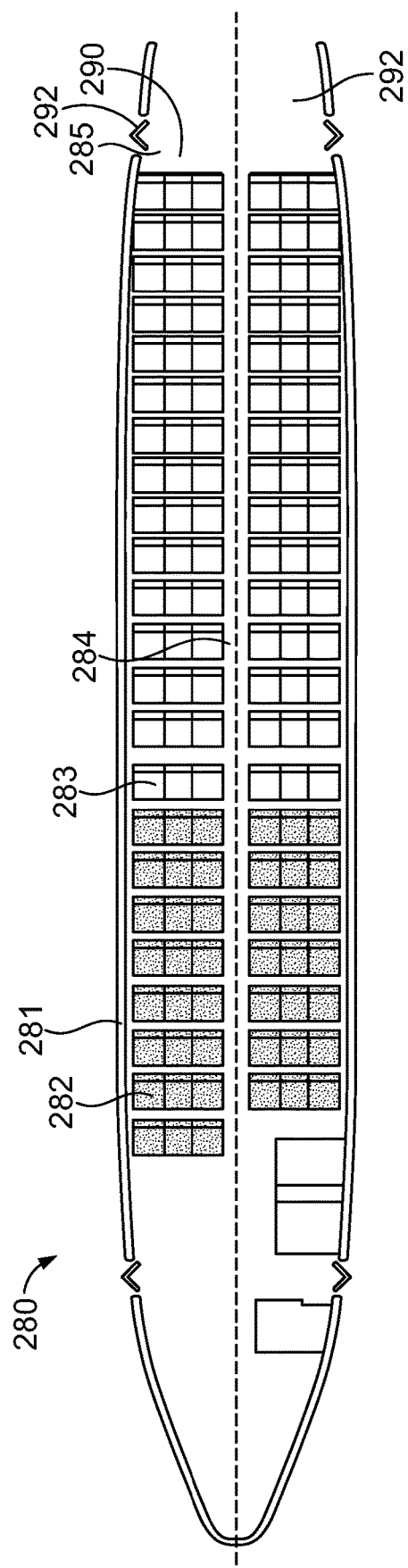
FIG. 2B illustrates a top plan view of an internal cabin of an aircraft, according to another embodiment of the present disclosure.

FIG. 2B illustrates a top plan view of an internal cabin 80 of an aircraft, according to another embodiment of the present disclosure. The internal cabin 80 may be within the fuselage 18 of the aircraft 10 shown in FIG. 1. For example, one or more fuselage walls may define the internal cabin 80. The internal cabin 80 includes multiple sections, including a main cabin 82 having passenger seats 83 and an aisle 84, and an aft section 85 behind the main cabin 82. The internal cabin 80 also includes a lavatory 87. The internal cabin 80 may include more or less sections than shown.

The internal cabin 80 has a single aisle 84 that extend a substantial length of the internal cabin 80 and lead to the aft section 85. The aisle 84 may extend through the center of the internal cabin 80 such that the aisle 284 is coaxial with a central longitudinal plane 86 of the internal cabin 80. The aisle 84 extends to egress paths or door passageways 90, which are areas adjacent to entrances of the aircraft. Exit doors 92 are located at ends of the egress paths 90. The egress paths 90 may be perpendicular to the aisle 84. The sanitizing system described herein may be used to sanitize air and various structures within the internal cabin 80.

Figure 3:
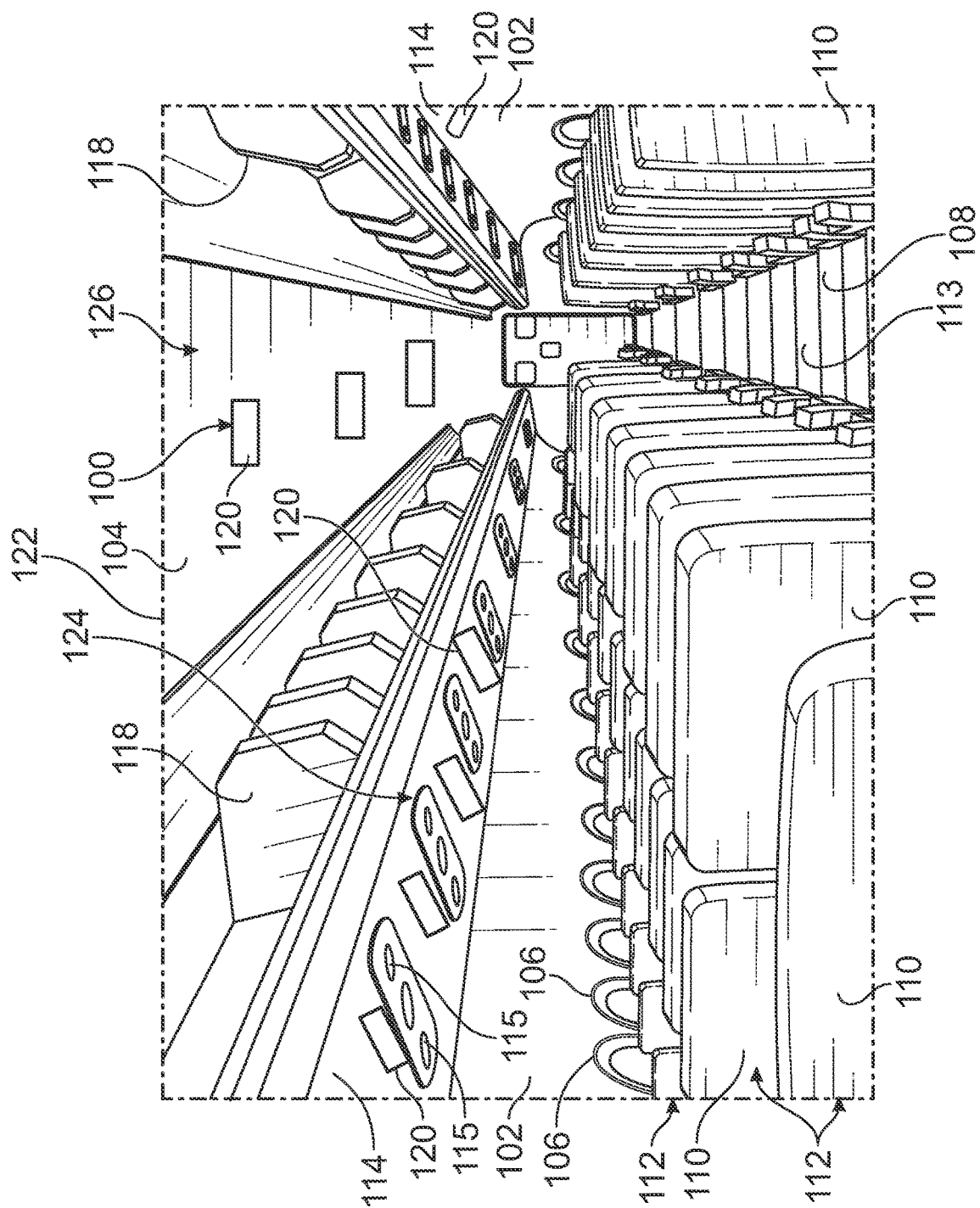
FIG. 3 illustrates a perspective view of a sanitizing system within a portion of an internal cabin of an aircraft according to an embodiment of the present disclosure.

FIG. 3 illustrates a perspective view of a sanitizing system 100 within a portion of an internal cabin 122 of an aircraft according to an embodiment of the present disclosure. The internal cabin 122 can represent either of the internal cabins 30, 80 shown in FIGS. 2A and 2B, respectively. The internal cabin 122 includes outboard walls 102 connected to a ceiling 104. Windows 106 may be formed within the outboard walls 102. A floor 108 supports rows of seats 110. A row 112 may include three seats 110 on either side of an aisle 113. However, the row 112 may include more or less seats 110 than shown. Additionally, the internal cabin 122 may include more than the single aisle 113 shown in FIG. 2.

Passenger service units (PSUs) 114 are secured between the outboard wall 302 and the ceiling 104 on either side of the aisle 113. The PSUs 114 are arranged in longitudinal columns that extend between a front end and rear end of the internal cabin 122. For example, at least one PSU 114 may be positioned over the seats 110 within a row 112 on either side of the aisle 113. The PSUs 114 may include personal air blowers 115 (e.g., or vents, puffers, etc.), reading lights, oxygen bag drop panels, attendant request buttons, and other such controls and components. At least some of the controls and components of the PSU 114 may be shared between groups of two or three seats 110 in the row 112, such as the reading light. Other components may be specific to individual seats 110, such as the personal air blowers 115.

Overhead stowage bin assemblies 118 are secured to the ceiling 104 and/or the outboard wall 102 above the PSU 114 on either side of the aisle 113. The overhead stowage bin assemblies 118 are secured over the seats 110. The overhead stowage bin assemblies 118 are configured to be pivoted open in order to receive passenger carry-on baggage and personal items, for example. As used herein, the term "outboard" means a position that is further away from a central longitudinal plane of the internal cabin 122 as compared to another component, and the term "inboard" means a position that is closer to the central longitudinal plane of the internal cabin 122 as compared to another component.

The sanitizing system 100 includes a plurality of ultraviolet (UV) lamps 120 mounted within the internal cabin 122. The UV lamps 120 are controlled to generate and emit UV light into the internal cabin 122 to sanitize and disinfect air and surfaces within the internal cabin 122. The UV lamps 120 may be located at various areas throughout the internal cabin 122. In the illustrated embodiment, a first subset 124 of UV lamps 120 are mounted to the PSUs 114 above the passenger seats 110, and is referred to herein as a PSU subset 124. For example, the UV lamps 120 in the PSUs 114 may be disposed proximate to other components of the PSUs 114, such as the air blowers 115 and the reading lights. In an embodiment, the UV lamps 120 in the PSU subset 124 are integrated into the PSUs 114 such that each UV lamp 120 emits UV light into an associated row 112 of seats 110 on one side of the aisle 113. Depending on the field of illumination or spread at which the UV light is emitted from each UV lamp 120, each PSU 114 may include only one or multiple UV lamps 120. The field of illumination refers to refers to a three-dimensional volume in space that is defined by the propagation of UV light waves (e.g., rays) emitted by the UV lamp 120. The width of the field of illumination can depend on mechanical features of the UV lamp 120, such as reflectors, collimators, lenses, and the like, and optionally may be set to provide a predetermined width. In a non-limiting embodiment, the field of illumination of the UV lamps 120 in the PSUs 114 may be sufficient for each UV lamp 120 to sanitize the air and surfaces around two passenger seats 110. Thus, for groups of three or more seats 110 in a row 112 on one side of the aisle 113, the PSU 114 may include at least two UV lamps 120 with one UV lamp 120 located outboard of another UV lamp 120 to enable the combined UV light to cover the entire group of seats 110 and the passengers seated thereon. In another non-limiting embodiment, the number of UV lamps 120 in the PSU subset 124 may match the total number of seats 110 such that each UV lamp 120 is specifically directed to and associated with a different seat 110 in the internal cabin 122.

A second subset 126 of UV lamps 120 of the sanitizing system 100 is mounted to the ceiling 104 between the overhead stowage bin assemblies 118. The UV lamps 120 in the second subset 126 are referred to as an aisle subset 126 because the UV lamps 120 emit UV light into the aisle 113. The aisle subset 126 is aligned in a linear column that extends a length of the internal cabin 122 between the front and rear ends. The UV lamps 120 in the aisle subset 126 are spaced apart. The spacing distance may be based on the field of illumination or spread of the UV light to ensure that there is at least some overlap in the coverage areas of two adjacent UV lamps 120 at a designated height above the floor 108 to avoid creating dead zones that could harbor pathogens.

Although two subsets 124, 126 or groupings of UV lamps 120 are shown in FIG. 2, the UV lamps 120 may be located in other areas of the cabin 122 as well, such as in galleys, in lavatories, at partitions between sections, and the like.

Figure 4:
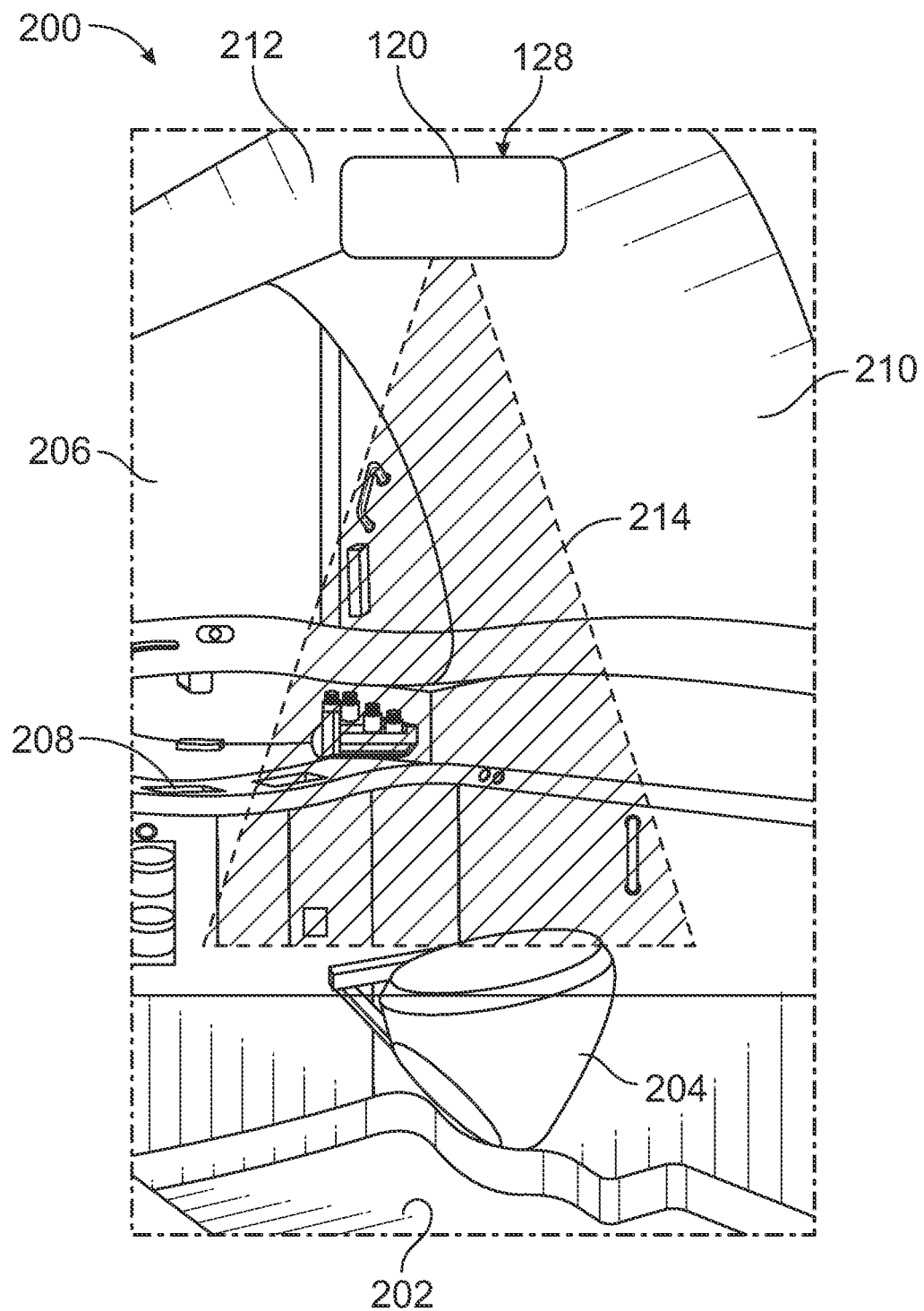
FIG. 4 illustrates a perspective internal view of a lavatory within an internal cabin of a vehicle.

FIG. 4 illustrates a perspective internal view of a lavatory 200 within an internal cabin of a vehicle, such as any of the internal cabins described herein. For example, the lavatory 200 may be any of the lavatories 45 shown in FIG. 2A or the lavatory 87 shown in FIG. 2B. The lavatory 200 includes a floor 202, a toilet 204, a mirror 206, a sink 208, walls 210, a ceiling 212, and a door (not shown) for establishing privacy. A UV lamp 120 of the sanitizing system 100 is located within the lavatory 200. The UV lamp 120 represents a third subset 128 of the UV lamps 120 of the sanitizing system 100, referred to herein as a lavatory subset 128. In alternative embodiment, the lavatory subset 128 may include more than the single UV lamp 120 depicted in FIG. 4. The UV lamp 120 is configured to emit UV light into the lavatory 200 to sanitize the air and surfaces.

Figure 5:
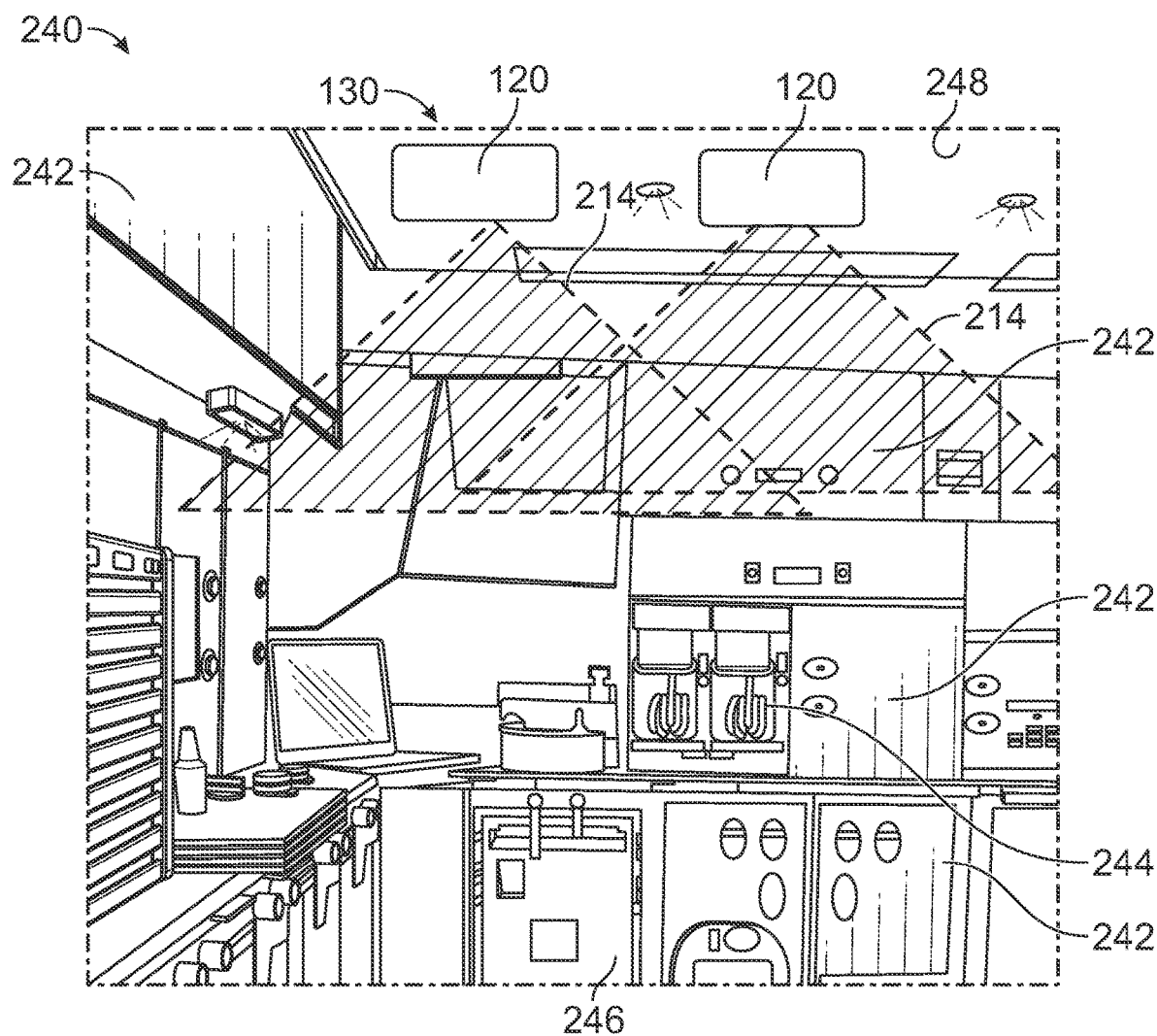
FIG. 5 illustrates a perspective view of a galley within an internal cabin of a vehicle.

FIG. 5 illustrates a perspective view of a galley 240 within an internal cabin of a vehicle, such as any of the internal cabins described herein. The galley 240 includes various cabinets 242 and appliances, such as a coffee maker 244. The galley 240 also includes a galley cart 246. The galley 240 may be occupied by crew members when preparing food and drinks for passengers, disposing of trash, and the like. Some crew members may sit in the galley during takeoff and landing stages of a trip. Passengers walk through or past the galley during boarding and deboarding. In the illustrated embodiment, two UV lamps 120 of the sanitizing system 100 are located within the galley 240 and positioned to emit UV light into the galley 240. The UV lamps 120 represent a galley subset 130 of the UV lamps 120 in the sanitizing system 100. Both UV lamps 120 are mounted along a ceiling 248 of the galley 240. The UV lamps 120 may be spaced apart such that fields of illumination 214 of the two UV lamps 120 partially overlap to provide substantial disinfection coverage of the galley 240.

Referring collectively to FIGS. 3-5, the UV lamps 120 of the sanitizing system 100 are positioned throughout the cabin 122 to maximize the coverage area of the UV light. Maximizing the coverage area refers to emitting UV light to cover a substantial amount or percentage of the area or volume within the cabin 122, such as over 80%, over 90%, over 95%, or the like, particularly in areas occupied and trafficked by passengers and crew. The UV light sanitizes and disinfects the air and surrounding surfaces. The surrounding surfaces that can be disinfected by the UV light can include the seats 110 (including arm and headrests thereof), skin and clothing of the passengers and crew, walls, doors, toilets, handwashing stations, drawers, appliances, and the like. The sanitizing system 100 is configured to persistently operate at least some of the UV lamps 120 in the on, emitting state even in the presence of passengers, such as during boarding, taxiing, flight, and deboarding. Unlike current practices which only provide intermittent disinfection, such as chemically cleaning the cabin 122 between flights and filtering a given volume of air every time that volume of air is pulled through a return register of an environmental control system, the sanitizing system 100 disinfects pathogens on surfaces and in the air on a continuous basis.

In an embodiment, the UV light emitted by the UV lamps 120 is controlled to enable the occupants (e.g., passengers and crew) to be exposed to the UV light for a prolonged period of time without harm. For example, the emitted UV light may have a designated wavelength or a narrow band of wavelengths experimentally determined to be harmless to human tissue through prolonged exposure. Thus, even if the UV lamps 120 persistently emit UV light through the duration of the flight, the passengers would be unharmed. The UV lamps 120 may be configured or constructed to only generate the designated wavelength or the narrow band. Alternatively, a filter may be utilized that absorbs or dissipates wavelengths outside of the designated wavelength or the narrow band such that emitted UV light in the field of illumination only consists of the designated wavelength or the narrow band.

In a non-limiting example, the designated wavelength is 222 nm. It has been found that sanitizing UV light having a wavelength of 222 nm kills pathogens (such as viruses and bacteria), instead of inactivating pathogens. In contrast, UVC light at a wavelength of 254 nm inactivates pathogens by interfering with their DNA, resulting in temporary inactivation, but may not kill the pathogens. Instead, the pathogen may be reactivated by exposure to ordinary white light at a reactivation rate of about 10% per hour. As such, UVC light at a wavelength of 254 nm may be ineffective in illuminated areas, such as within an internal cabin of a vehicle. Moreover, UVC light at 254 nm is not recommended for human exposure because it may be able to penetrate human cells. In contrast, sanitizing UV light having a wavelength of 222 nm is safe for human exposure and kills pathogens. Further, the sanitizing UV light having a wavelength of 222 nm may be emitted at full power within one millisecond or less of the UV lamps 120 being activated (in contrast the UVC light having a wavelength of 254 nm, which may take seconds or even minutes to reach full power).

Figure 6:
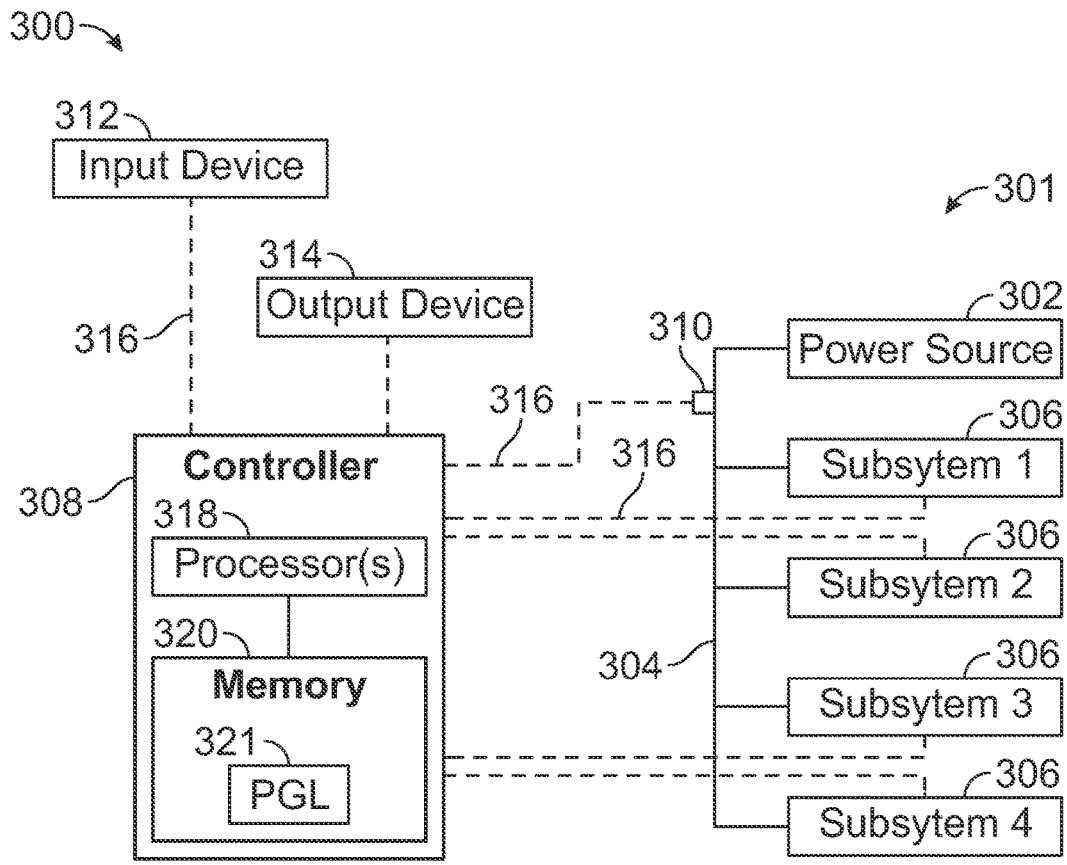
FIG. 6 is a schematic diagram of a power management system onboard a vehicle according to an embodiment.

FIG. 6 is a schematic diagram of a power management system 300 onboard a vehicle according to an embodiment.

The vehicle may be an aircraft, such as the aircraft 10 shown in FIG. 1. The power management system 300 is associated with a power delivery system 301 onboard the vehicle. The power delivery system 301 includes a power source 302, a power bus 304, and multiple subsystems 306. The subsystems 306 have electrical devices and equipment that utilizes electrical power supplied by the power source 302. The power source 302 can include one or more generators that generate electrical energy from mechanical energy. The power source 302 can be referred to as a power generation system. The power bus 304 is one or more electrically conductive wires and/or cables that conduct electric current between the power source 302 and the subsystems 306. Each of the subsystems 306 are electrically connected to the bus 304 and can receive electrical power from the power source 302 via the bus 304. The subsystems 306 may be connected in parallel to the bus 304. There are four subsystems 306 shown in FIG. 6, but there may be more or less than four subsystems 306 in other embodiments. The subsystems 306 represent non-essential systems. Non-limiting examples of possible subsystems 306 include the sanitizing system 100 shown in FIGS. 3-5, galley appliances (e.g., ovens, chillers, coffee makers, and the like), PSU devices (e.g., back-of-headrest displays, personal lights, and the like), lavatory devices, general cabin interior lighting, and certain non-essential portions of an environmental control system, such as an air conditioning cycle and/or air blowing system.

The power management system 300 according to an embodiment includes a controller 308, a sensor 310, an input device 312, and an output device 314. The controller 308 is operatively connected to the sensor 310, the input device 312, and the output device 314 via wired and/or wireless communication pathways 316. The controller 308 generates messages in the form of electrical signals that are communicated to the subsystems 306 to manage the power delivery and consumption of the vehicle. The messages that are generated may be based on signals (e.g., data) received from the sensor 310. The controller 308 represents hardware circuitry that includes and/or is connected with one or more processors 318 (e.g., one or more microprocessors, integrated circuits, microcontrollers, field programmable gate arrays, etc.). The controller 308 includes and/or is connected with a tangible and non-transitory computer-readable storage medium (e.g., memory) 320. For example, the memory 320 may store programmed instructions (e.g., software) that is executed by the one or more processors 318 to perform the operations of the controller 308 described herein.

The input device 312 can represent or include a selector knob, a workstation computer, a tablet computer, a handheld computer (e.g., a smartphone), a keyboard, a touchpad, a joystick, and the like for enabling an operator to control the power management system 300. For example, an operator can enter a user input via the input device 312 for ranking the subsystems 306 in terms of priority, as described below, and updating a predetermine ranking. The output device 314 can be an integrated display device onboard the aircraft and/or a display screen on a personal computer, tablet, or handheld computer (e.g., smartphone). The controller 308 may generate control signals for controlling the output device 314 to display notification to operators, such as to notify an operator that one or more of the subsystems 306 is being operated at reduced power due to a detected deficit in the power budget.

The controller 308 of the power management system 300 monitors the power on the bus 304. The power on the bus 304 represents the electrical power that is supplied by the power source 302 to power the loads represented by the different subsystems 306. The power on the bus 304 may be dependent, at least in part, on the demanded power from the subsystems 306. For example, if all of the subsystems 306 are active, the demand or load may be greater than if half of the subsystems 306 are inactive and not drawing power from the bus 304. The controller 308 may monitor the power on the bus 304 via the sensor 310, which measures one or more properties of the electrical energy on the bus 304. For example, the sensor 310 may measure voltage, current, and the like, and may generate sensor signals indicative of the measured properties. The controller 308 analyzes the sensor signals to monitor the current power on the bus 304.

The controller 308 determines when the power on the bus 304 exceeds a designated limit, referred to as a power generation limit 321. The power generation limit 321 may be predetermined and stored in the memory 320. The power generation limit 321 may be selected based on a capability of the power source, a desired energy efficiency of the vehicle, and/or the like. As the controller 308 receives updated measurements of the power on the bus 304, the controller 308 compares the power on the bus 304 to the designated power generation limit 321. If the power on the bus 304 exceeds the power generation limit 321, the controller 308 determines that there is a deficit in the power budget, meaning that more power is demanded than is available to supply for an extended period of time. The controller 308 may subtract the value of the power on the bus 304 from the power generation limit 321 to determine the deficit amount.

The controller 308 remedies the deficit in the power budget by generating a reduction command message that is communicated to one or more of the subsystems 306. Although not shown, the power management system 300 may include a separate communication device that includes hardware and circuitry for communicating messages between the controller 308 and the various subsystems 306. The communication system can include an antenna and transceiver for wireless messaging or may communicate via metal wires or optical fibers.

In an embodiment, the subsystems 306 are ranked in order of priority, and the ranking may be stored in the memory 320. For example, in FIG. 6, the subsystem 1 may be designated as the lowest priority, followed by the subsystem 2, the subsystem 3, and finally the subsystem 4, which is the highest priority. The ranking order may be predetermined, such as input by an operator using the input device 312. In a non-limiting example, the lowest-priority subsystem 306 (e.g., subsystem 1) may be the sanitizing system 100 that includes UV lamps 120 in various locations of the internal cabin 122, as shown in FIGS. 3-5. Another low-priority subsystem 306 may be the various appliances in the galley 240, such as the coffee maker 244, oven, refrigerator, chiller, and the like. In an embodiment, the controller 308 commands the subsystems 306 to reduce the respective power demand on the bus 304 in order based on priority, starting with the lowest-priority subsystem and then working up the chain, as necessary, until the deficit is remedied (e.g., the power on the bus 304 is sufficiently below the generation limit 321). For example, in response to determining that there is a deficit of 10 kw (e.g., the power generation limit 321 is exceeded by 10 kW), the controller 308 may generate a command message that is communicated to the lowest-priority subsystem 306. The command message may instruct the recipient subsystem 306 to reduce the load on the bus 304 by the deficit amount, in this case 10 kW.

In response the lowest-priority subsystem 306 attempts to comply with the command by reducing the power supplied to one or more components or one or more subsets of components in the respective subsystem 306. The controller 308 subsequently may receive a reply message from the lowest-priority subsystem 306 that indicates the adjusted load or draw of the subsystem 306 after the reduction process. Based on the reply message and updated sensor signals from the sensor 310, the controller 308 determines if the deficit is remedied. The deficit is remedied once the power reduction in the subsystems 306 causes the power on the bus 304 to be below the power generation limit 321. Optionally, the deficit may be considered remedied or satisfied once the power on the bus 304 falls below a clearance threshold that is less than the power generation limit 321. Reducing the load until the clearance threshold is passed prevents a situation where the power management system 300 repetitively crosses the power generation limit 321, which can be taxing on the controller 308 and other components of the system 300.

Once the deficit is remedied, the controller 308 may once again allow all subsystems 306 to operate normally without artificially limiting power usage. If, on the other hand, instructing the lowest-priority subsystem 306 to reduce power does not remedy the deficit, the controller 308 may communicate a reduction command message to the second lowest-priority subsystem 306. For example, if the deficit amount is 10 kW, and the lowest-priority subsystem 306 can only reduce the load by 7 kW, then the command message communicated to the second lowest-priority subsystem 306 may instruct a reduction of 3 kW. Optionally, the lowest-priority subsystem 306 may completely deactivate before the second lowest-priority subsystem 306 is requested to reduce power consumption.

In an embodiment, if the deficit is 10 kW and the lowest-priority subsystem 306 is currently drawing 15 kW from the bus 304, then the lowest-priority subsystem 306 reduces the load by 10 kW to comply with the instructions. The lowest-priority subsystem 306 may continue to operate at least some of the components thereof at diminished power levels such that the total load of the subsystem 306 is no greater than 5 kW. Thus, the subsystems 306 are controlled, based on a priority ranking, to reduce the load on the bus 304 proportionate to the deficit amount. The lower-priority subsystems 306 may continue functioning at lower power levels rather than merely deactivate, to avoid complete disruption of service.

Figure 7:
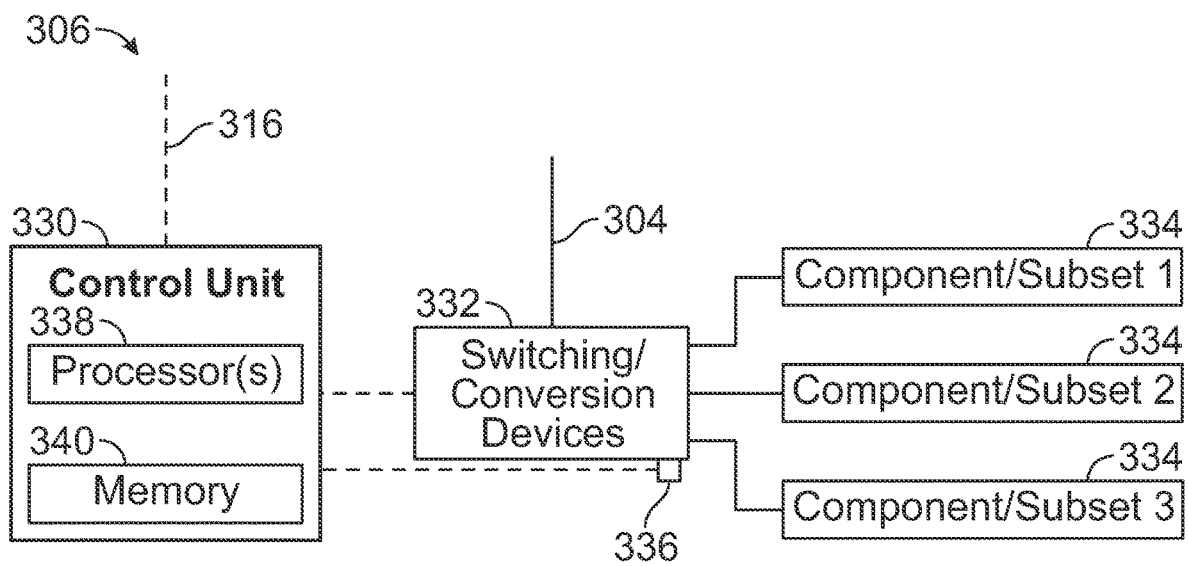
FIG. 7 is a schematic diagram of one of the subsystems of the vehicle according to an embodiment.

FIG. 7 is a schematic diagram of one of the subsystems 306 of the vehicle according to an embodiment. The subsystem 306 includes a control unit 330, switching devices and/or power conversion devices 332, multiple components or subsets of components 334, and optionally a sensor 336. The control unit 330 is operatively connected to the switching devices and/or power conversion devices 332 and the sensor 336, and is also operatively connected via the communication path 316 to the controller 308 shown in FIG. 6. The control unit 330 represents hardware circuitry that includes and/or is connected with one or more processors 338 (e.g., one or more microprocessors, integrated circuits, microcontrollers, field programmable gate arrays, etc.). The control unit 330 includes and/or is connected with a tangible and non-transitory computer-readable storage medium (e.g., memory) 340. For example, the memory 340 may store programmed instructions (e.g., software) that is executed by the one or more processors 338 to perform the operations of the control unit 330 described herein. The subsystem 306 shown in FIG. 7 can represent any of the subsystems 306 in FIG. 6.

The switching devices and/or power conversion devices 332 are configured to selectively control the amount of power supplied to each of the components/subsets of components 334. For example, the switching devices and/or power conversion devices 332 can include one or more solid-state relays, electromechanical relays, optical switches, power converters (e.g., DC-to-DC, DC-to-AC), and/or the like. The sensor 336 can measure one or more characteristics of the electrical power supplied to the components/subsets 334 to enable the control unit 330 to determine the load of the subsystem 306 on the power bus 304 at a given time.

In an embodiment, the components/subsets 334 in the subsystem 306 are ranked based on priority, similar to the subsystems 306 shown in FIG. 6. The ranking may be predetermined and stored in the memory 340. Optionally, the ranking can be updated by an operator using the input device 312 or another input device. Upon receiving a reduction command message from the controller 308, the control unit 330 of the subsystem 306 generates a control signal to the switching and/or conversion devices 332 to control the devices 332 to reduce the power that is supplied to one or more of the lower-priority components or subsets of components 334. For example, the control signal may reduce power supplied to the lowest-priority component/subset 334 first. If the deficit is larger than the load of the lowest-priority component/subset 334, then the control unit 330 may deactivate the lowest-priority component/subset 334 and then control the switching and/or conversion devices 332 to reduce the power supplied to the second lowest-priority component/subset 334. The control unit 330 can work up the chain of priority until the deficit is remedied or all of the components/subsets 334 in the subsystem 306 are deactivated, whichever comes first. The control unit 330 may generate a reply message for communication to the controller 308 indicating the amount of power reduction accomplished by the subsystem 306.

For the subsystem 306 that represents sanitizing system 100 shown in FIGS. 3-5, the components and/or subsets of components 334 can represent the different subsets of UV lamps 120 throughout the internal cabin 122. For example, the PSU subset 124 of UV lamps 120 above the seats 110 in FIG. 3 can represent one subset of components 334, the aisle subset 126 in FIG. 3 can represent another subset 334, the lavatory subset 128 in FIG. 4 can represent another subset 334, and the galley subset 130 in FIG. 5 can represent still another subset 334. In an embodiment, the sanitizing system 100 is one of the lower-priority subsystems 306. Optionally, the sanitizing system 100 is the lowest-priority subsystem 306.

The priority ranking of the subsets 334 can depend on various factors, such as user inputs, time of day, stage of the trip, susceptibility of the passengers, occupancy by the passengers, and the like. For example, during takeoff and landing of an aircraft, the lavatory 200 may be off-limits, so the lavatory subset 128 of UV lamps 120 may be ranked the lowest priority subset 334 of the sanitizing system 100 during takeoff and landing. As a result, the UV lamp 120 in the lavatory 200 may be the first UV lamp 120 to experience reduced power in case of a deficit in the power budget during takeoff and landing. During cruise flight, though, rapidly sanitizing the lavatory 200 between uses may be deemed more of a priority than sanitizing the galley 240 or the aisle 113, for example. For example, during cruise flight, the galley subset 130 of UV lamps 120 may be ranked lower priority than the aisle subset 126, which in turn is lower than the PSU subset 124 and the lavatory subset 128.

In another example, the UV lamps 120 in some common areas that are periodically occupied by different passengers may be ranked as lower priority than the UV lamps 120 in the PSU units 114, because the PSU subset 124 persistently sanitizes the air and surfaces around passengers in their seats 110, which is the location of the passengers for at least most of the flight. In a non-limiting example, in response to receiving a power reduction command from the controller 308 during flight, the sanitizing system 100 may first reduce power to the galley subset 130, then to the aisle subset 126, then to the lavatory subset 128, and finally the PSU subset 124. If the deficit is 10 kW and that power exceeds the draw of the UV lamps 120 in the galley 240, the control unit 330 may deactivate the galley subset 130 of UV lamps 120. If the remaining balance of the deficit is 6 kW, for example, after deactivating the galley subset 130, the control unit 330 reduces the power supplied to the next lowest-priority subset, such as the aisle subset 126. If the aisle subset 126 draws 8 kW, the control unit 330 reduces the power supplied to the aisle subset 126 to 2 kW in order to remedy the deficit while continuing to allow the UV lamps 120 along the aisle 113 to emit UV light.

The switching and power conversion devices 332 are used to modulate the power supplied to the UV lamps 120. Even at a low power level, the UV lamps 120 can still emit UV light that kills or neutralizes pathogens, but the dose (e.g., intensity and/or range) of the UV light is reduced, yielding less antimicrobial effectiveness per unit time.

Optionally, even the subsets 124, 126, 128, 130 of UV lamps 120 described herein can be sub-portioned and ranked based on priority. For example, some UV lamps 120 in the PSU subset 124 can be ranked higher priority than other UV lamps 120 in the same subset 124. In a non-limiting example, if it is determined that a passenger seat 110 is unoccupied, the associated UV lamp 120 in the PSU subset 124 may be classified as having a low priority, such as the lowest priority of the UV lamps 120. The open seat 110 can be determined based on sensor signals received from a pressure sensor, proximity sensor, of the like. On the other hand, if it is determined that a seat 110 or group of seats 110 is occupied by passengers that are immunosuppressed or particularly susceptible to pathogens than other passengers, the UV lamps 120 associated with those seats 110 are reclassified as having high priority, such as the highest priority of the UV lamps. As a result, the first UV lamps 120 of the PSU subset 124 that may experience reduced power may be the lamps 120 above open seats 110, and the last UV lamps 120 that may be reduced are the lamps 120 above passengers more susceptible to illness from pathogens, such as elderly passengers, passengers with underlying health issues, and the like. It may be possible for such passengers to positively self-identify to the vehicle crew that the passengers are susceptible and would like increased sanitization.

Figure 8:
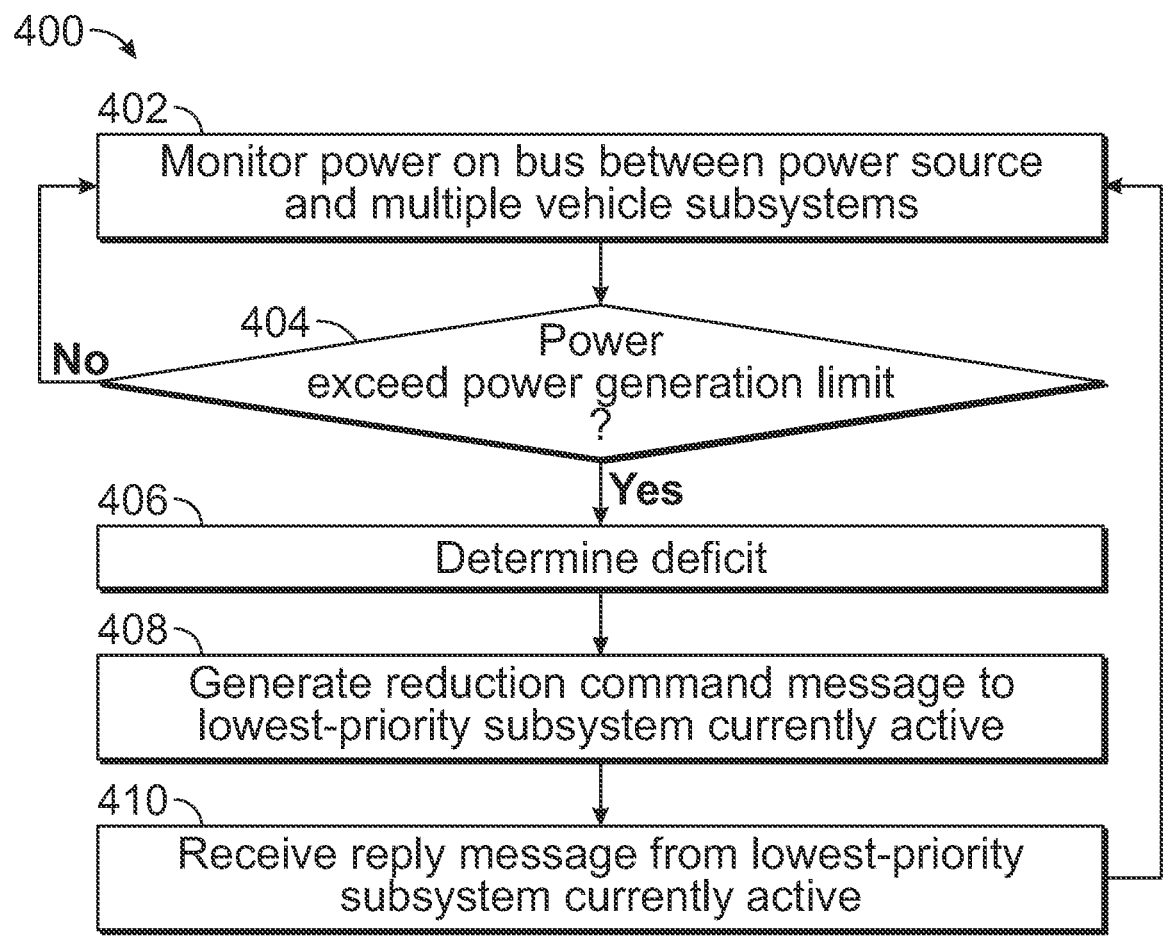
FIG. 8 is a flow chart of a method for managing the allocation of power among vehicle subsystems according to an embodiment.

FIG. 8 is a flow chart of a method 400 for managing the allocation of power among vehicle subsystems according to an embodiment. The method 400 may be performed by the power management system 300 described above. The method 400 can incorporate the sanitizing system 100 described above for sanitizing and disinfecting air and surface within an internal cabin of the vehicle by persistent emission of UV light. Certain steps of the method 400 may be performed by the controller 308 shown in FIG. 6 based on programmed logic or instructions. The method 400 optionally includes additional steps than described, fewer steps than described, and/or different steps than described.

At 402, power on a bus 304 between a power source 302 and multiple non-essential subsystems 306 of the vehicle is monitored, such as via one or more sensors 310. At 404, it is determined whether the power on the bus 304 exceeds a designated power generation limit 321 stored in a memory 320. If the power on the bus 304 does not exceed the power generation limit 321, flow returns to 402 for additional monitoring of the power on the bus 304. If, on the other hand, the power on the bus 304 exceeds the power generation limit 321, flow proceeds to 406 and a deficit in the power budget is determined. The deficit represents the difference between the power on the bus 304 and the power generation limit 321, and signifies the amount or extent the power on the bus 304 is excessive.

At 408, a reduction command message is generated for communication to a lowest-priority vehicle subsystem 306 that is currently active. The reduction command message instructs the recipient subsystem 306 to reduce power consumption by an amount equal to the deficit. The subsystem 306 modifies the power consumption in response as described with reference to FIG. 7. At 410, a reply message is received from the lowest-priority vehicle subsystem 306. The reply message indicates that the reduction command message was successfully received and that a reduction in power consumption was made by the subsystem 306. The reply message optionally may include a value representing the amount of the power reduction. The flow returns to 402 and the power on the bus 304 is again monitored and compared to the power generation limit 321 at 404. If the deficit has been remedied, then the answer at 404 is No. If the deficit has not been fully remedied, such that the power on the bus 304 still exceeds the power generation limit 321 after the reduction by the lowest-priority vehicle subsystem 306, then flow proceeds to 406 and 408 again. At 408, the previous lowest-priority vehicle subsystem 306 is now inactive, so a reduction command message is not generated for communication to the next lowest-priority sub system 306.

If any subsystem 306 that receives a reduction command message is able to remedy the deficit by reducing the power consumption by the amount of the deficit without deactivating all components of the subsystem 306, that subsystem is permitted and controlled to operate the components of the subsystem 306 at a reduce power level to avoid complete disruption in functionality of that subsystem 306 while enabling the power on the bus 304 to be maintained within the power generation limit 321.

Figure 9:
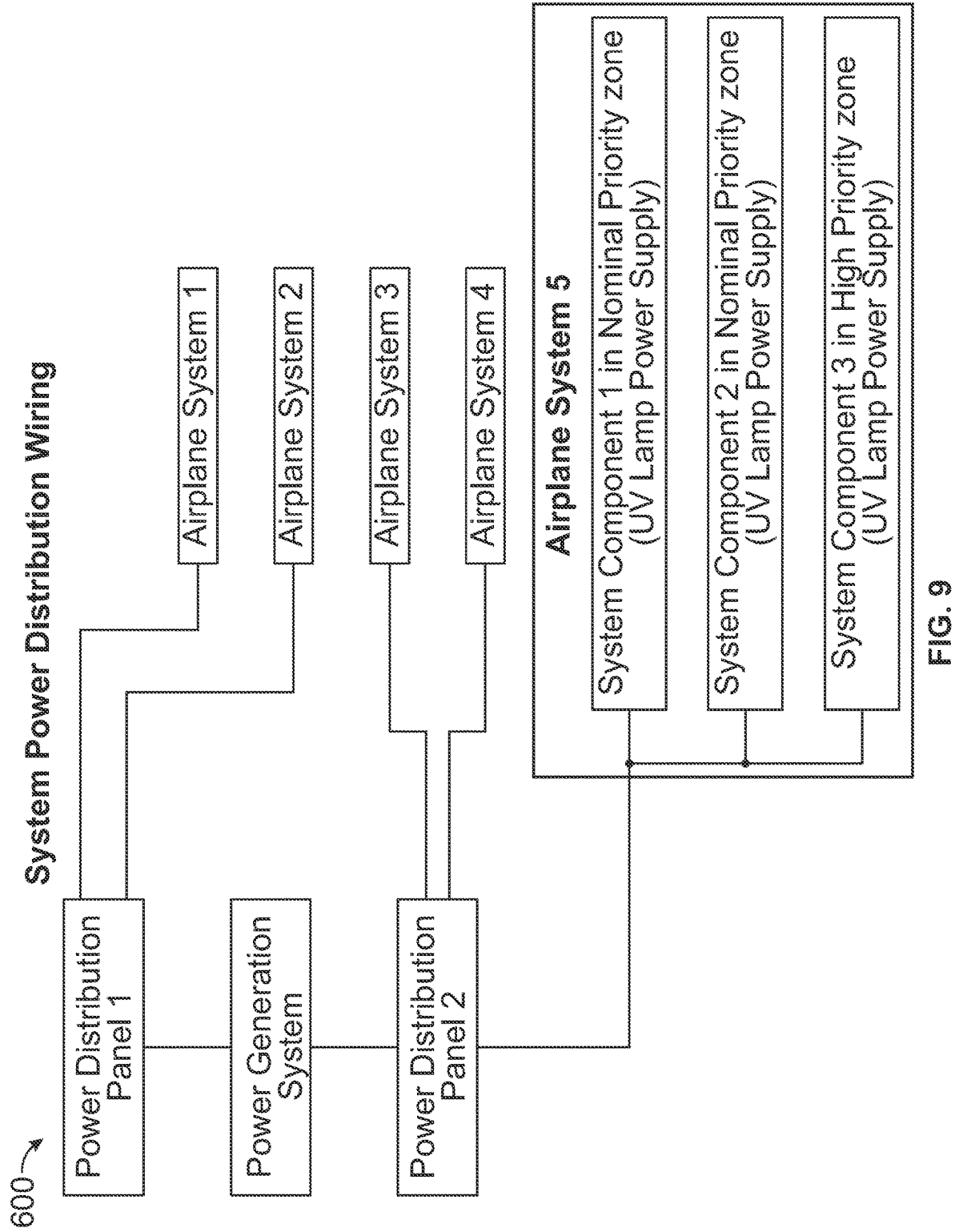
FIG. 9 illustrates a system power distribution wiring diagram of the power management system according to an embodiment.
Figure 10:
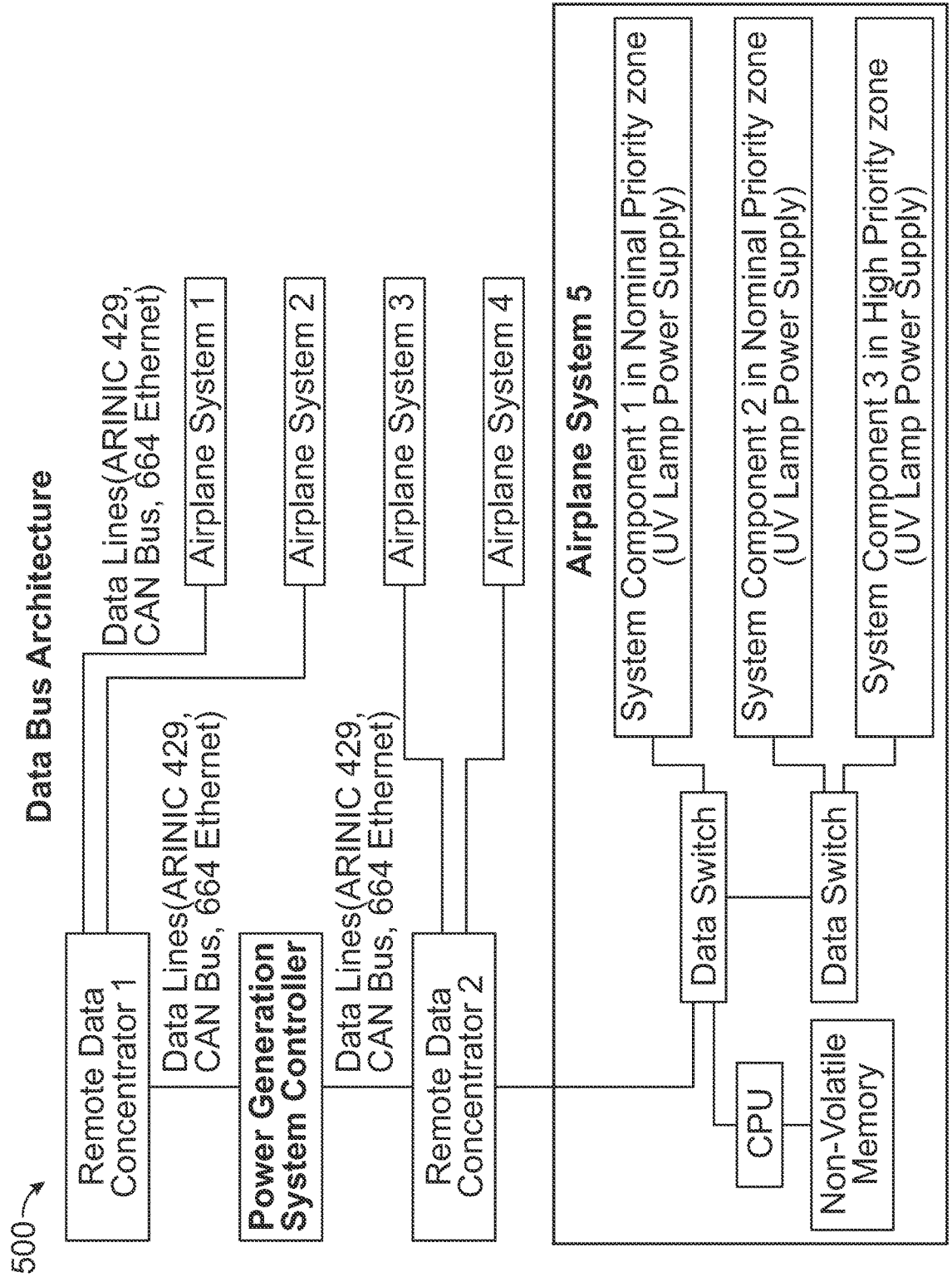
FIG. 10 illustrates a data bus architecture diagram of the power management system according to an embodiment.
Figure 11:
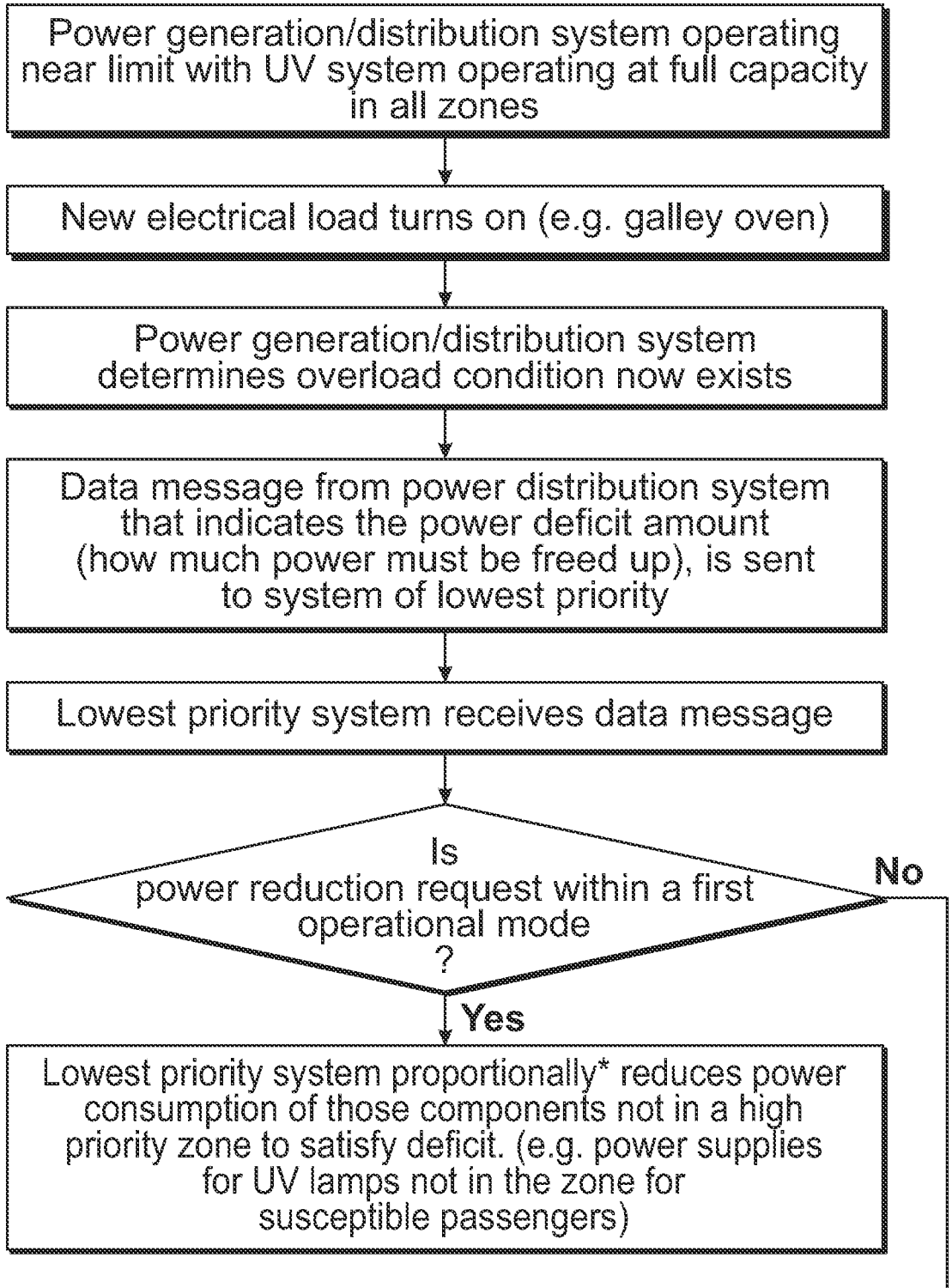
FIG. 11 is a flow chart of a method for managing the allocation of power among vehicle subsystems according to another embodiment.
Figure 11:
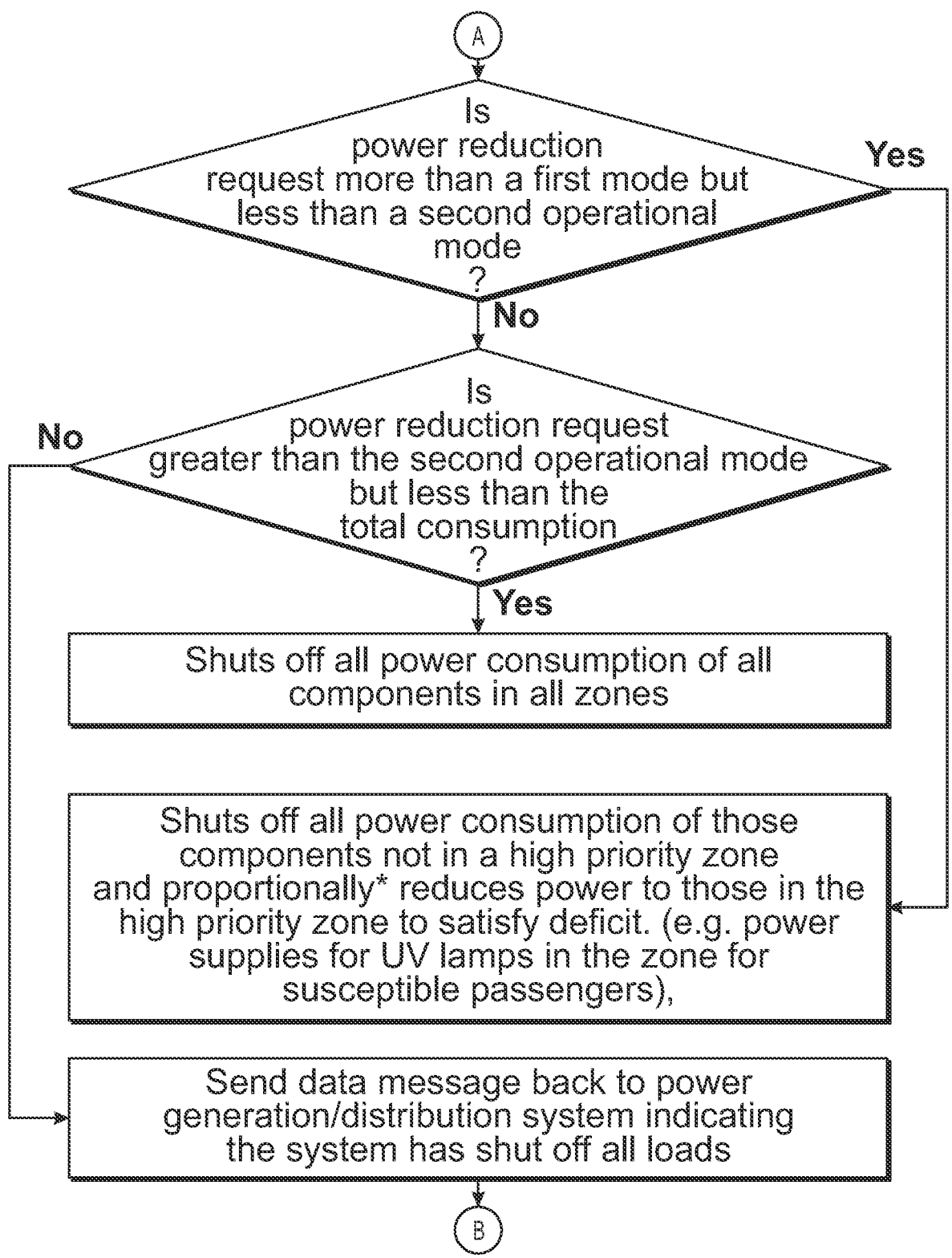
Figure 11:
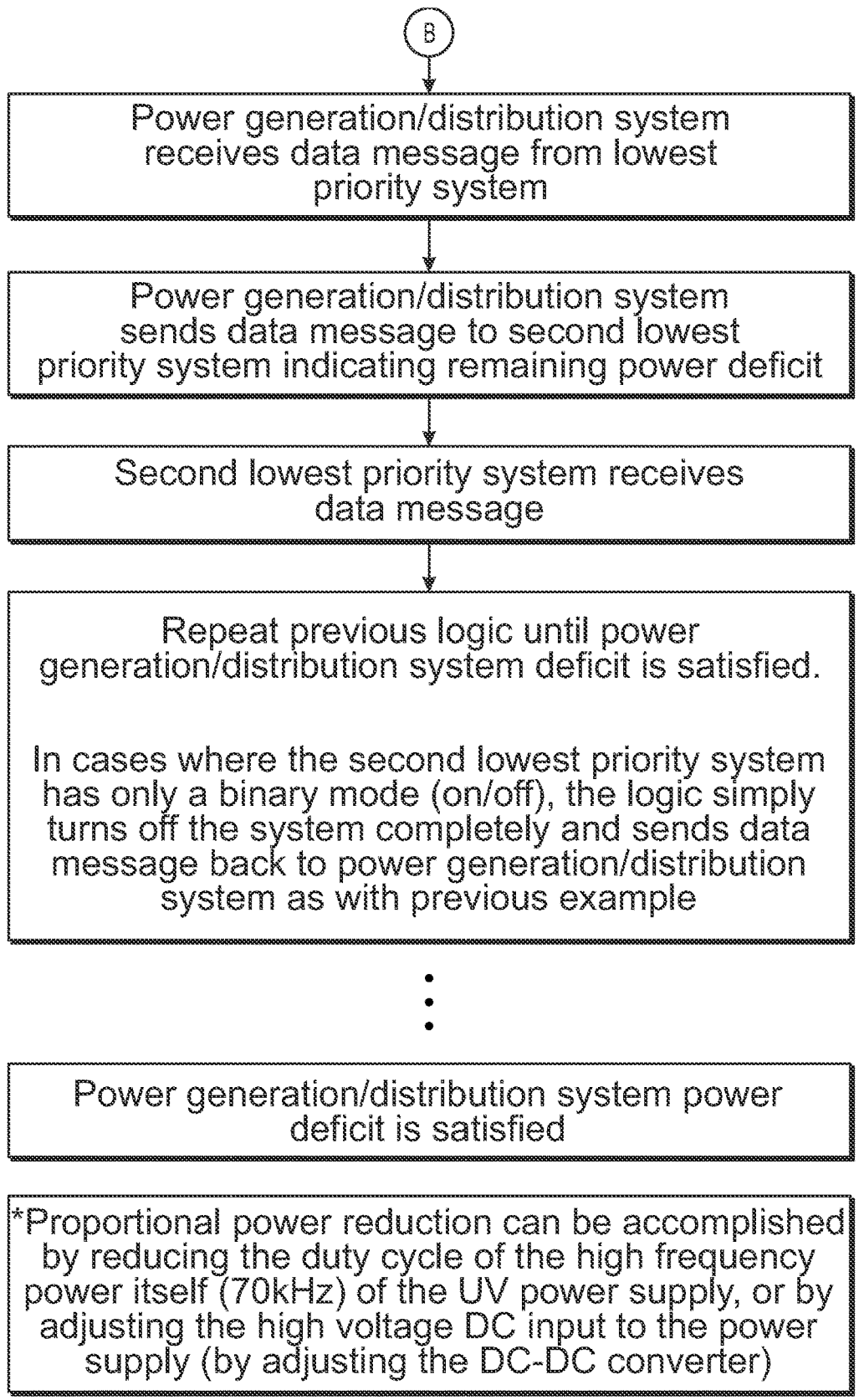

FIG. 9 illustrates a system power distribution wiring diagram 500 of the power management system 300 according to an embodiment. FIG. 10 illustrates a data bus architecture diagram 600 of the power management system 300 according to an embodiment. In FIGS. 9 and 10, the "Airplane System 5" represents the sanitizing system 100. FIG. 11 is a flow chart of a method 700 for managing the allocation of power among vehicle subsystems according to another embodiment.

As described herein, embodiments of the present disclosure provide systems and methods for sanitizing and disinfecting surfaces, air, and people within an internal cabin of a vehicle using UV light without harming the people exposed to the UV light. Further, embodiments of the present disclosure provide built-in, easy-to-use, and safe systems and methods for using UV light to sanitize air and surfaces within an internal vehicle cabin, and modulating the power draw of the UV lights to maintain a power generation limit onboard the vehicle.

The inventive subject matter is directed to an adaptable power management system that allows for systems to operate at a reduced function as needed to maintain the airplane level power generation limit. The system data bus architecture comprises a power generator system controller configured to monitor the power generation load, and communicate to the member systems that draw on those loads as capacity limits are reached. In operating conditions where sufficient power capacity is available, all systems would operate normally. When the capacity is exceeded, each member system would have a pre-programed priority ranking, and would proportionally respond to the decreased airplane load to equitably degrade the power of the UV lights based on the priority level. Then the member system communicates to the power generator system that the load has been adjusted. The logic cycle is repeated until the power deficit is satisfied. In cases where the member system of the lowest priority has only a binary (on/off mode), the power to that system turns off completely.

Further, the disclosure comprises embodiments according to the following clauses:

Clause 1. A power management system comprising:
a controller including one or more processors, the controller configured to monitor electrical power on a power bus of a vehicle, the power bus electrically connecting a power source to multiple subsystems of the vehicle for powering the subsystems via the electrical power on the power bus,
the controller further configured to determine that the electrical power on the power bus exceeds a designated power generation limit, and, in response, generate a reduction command message for communication to a lowest-priority subsystem of the subsystems, the reduction command message instructing the lowest-priority subsystem to reduce power consumption.

Clause 2. The power management system of Clause 1, wherein the controller is configured to determine a deficit between the electrical power on the power bus and the designated power generation limit, and is configured to include the deficit in the reduction command message.

Clause 3. The power management system of Clause 1 or 2, wherein, responsive to determining that the electrical power on the power bus still exceeds the designated power generation limit after generating the reduction command message, the controller is configured to generate a second reduction command message for communication to a next lowest-priority subsystem of the subsystems.

Clause 4. The power management system of any of Clauses 1-3, wherein the controller is configured to access a ranking of the subsystems in a memory device to determine the lowest-priority subsystem.

Clause 5. The power management system of any of Clauses 1-4, wherein the subsystems are non-essential to safe operation of the vehicle.

Clause 6. The power management system of any of Clauses 1-5, wherein the subsystems include one or more of a sanitizing system, a galley system, a lavatory system, a passenger service unit system, and an interior lighting system.

Clause 7. The power management system of any of Clauses 1-6, wherein the lowest-priority subsystem is a sanitizing system that includes a plurality of ultraviolet (UV) lamps mounted at various locations within an internal cabin of the vehicle, wherein the UV lamps are configured to receive electrical power from the power bus and emit UV light into the internal cabin.

Clause 8. The power management system of Clause 7, wherein the sanitizing system further includes a control unit including one or more processors, and, responsive to receiving the reduction command message, the control unit is configured to reduce an amount of power supplied to one or more of the UV lamps without causing the one or more UV lamps to cease emitting UV light.

Clause 9. The power management system of Clause 8, wherein the control unit of the sanitizing system is configured to reduce the amount of power supplied to a first subset of the UV lamps prior to or instead of reducing the power supplied to a different, second subset of the UV lamps based on the first subset having a lower priority ranking than the second subset.

Clause 10. The power management system of Clause 7, wherein the UV lamps are configured to emit the UV light at a designated wavelength or narrow wavelength range that is safe for human tissue.

Clause 11. The power management system of Clause 10, wherein the designated wavelength is 222 nm.

Clause 12. The power management system of any of Clauses 1-11, further comprising a sensor operatively connected to the controller and configured to measure one or more characteristics of the electrical power on the power bus, the controller configured to monitor the electrical power on the power bus based on sensor signals from the sensor.

Clause 13. The power management system of any of Clauses 1-12, wherein the vehicle is an aircraft.

Clause 14. A method comprising:
monitoring, via a controller including one or more processors, electrical power on a power bus of a vehicle, the power bus electrically connecting a power source to multiple subsystems of the vehicle for powering the subsystems via the electrical power on the power bus; and
responsive to determining that the electrical power on the power bus exceeds a designated power generation limit, generating a reduction command message for communication to a lowest-priority subsystem of the subsystems, the reduction command message instructing the lowest-priority subsystem to reduce power consumption.

Clause 15. The method of Clause 14, further comprising determining a deficit between the electrical power on the power bus and the designated power generation limit, wherein the reduction command message is generated to include the deficit.

Clause 16. The method of Clause 14 or 15, further comprising again monitoring the electrical power on the power bus after generating the reduction command message for communication to the lowest-priority subsystem, and, responsive to determining that the electrical power on the power bus still exceeds the designated power generation limit, generating a second reduction command message for communication to a next lowest-priority subsystem of the subsystems.

Clause 17. The method of any of Clauses 14-16, further comprising accessing a ranking of the subsystems in a memory device to determine the lowest-priority subsystem.

Clause 18. The method of any of Clauses 14-17, wherein the lowest-priority subsystem is a sanitizing system that includes a plurality of ultraviolet (UV) lamps mounted at various locations within an internal cabin of the vehicle and configured to emit UV light into the internal cabin using the electrical power on the power bus, wherein the method further comprises reducing an amount of power supplied to one or more of the UV lamps, based on the reduction command message, without causing the one or more UV lamps to cease emitting UV light.

Clause 19. The method of Clause 18, further comprising controlling the UV lamps to emit the UV light at a designated wavelength or narrow wavelength range that is safe for human tissue at prolonged exposure.

Clause 20. A power management system comprising:
- a controller including one or more processors, the controller configured to monitor electrical power on a power bus of a vehicle, the power bus electrically connecting a power source to multiple subsystems of the vehicle for powering the subsystems via the electrical power on the power bus; and
- a sanitizing system that represents one of the subsystems, the sanitizing system including a plurality of ultraviolet (UV) lamps mounted at various locations within an internal cabin of the vehicle and configured to emit UV light into the internal cabin using the electrical power on the power bus,
- the controller further configured to determine that the electrical power on the power bus exceeds a designated power generation limit, and, in response, generate a reduction command message for communication to the sanitizing system, the reduction command message instructing the sanitizing system to reduce power consumption,
- the sanitizing system configured to reduce an amount of power supplied to one or more of the UV lamps, based on the reduction command message, to diminish the UV light output from the one or more UV lamps without causing the one or more UV lamps to cease emitting UV light.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

As used herein, value modifiers such as "about," "substantially," and "approximately" inserted before a numerical value indicate that the value can represent other values within a designated threshold range above and/or below the specified value, such as values within 5%, 10%, or 15% of the specified value.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A power management system comprising:
- a controller including one or more processors, the controller configured to monitor electrical power on a power bus of a vehicle, the power bus electrically connecting a power source to multiple subsystems of the vehicle for powering the subsystems via the electrical power on the power bus,
- the controller further configured to determine that the electrical power on the power bus exceeds a designated power generation limit, and, in response, generate a reduction command message for communication to a lowest-priority subsystem of the subsystems, the reduction command message instructing the lowest-priority subsystem to reduce power consumption,
- wherein, responsive to determining that the electrical power on the power bus still exceeds the designated power generation limit after generating the reduction command message, the controller is configured to generate a second reduction command message for communication to a next lowest-priority subsystem of the subsystems.

2. The power management system of claim 1, wherein the controller is configured to determine a deficit between the electrical power on the power bus and the designated power generation limit, and is configured to include the deficit in the reduction command message.

3. The power management system of claim 1, wherein the controller is configured to access a ranking of the subsystems in a memory device to determine the lowest-priority subsystem.

4. The power management system of claim 1, wherein the subsystems are non-essential to safe operation of the vehicle.

5. The power management system of claim 1, wherein the subsystems include one or more of a sanitizing system, a galley system, a lavatory system, a passenger service unit system, and an interior lighting system.

6. The power management system of claim 1, wherein the lowest-priority subsystem is a sanitizing system that includes a plurality of ultraviolet (UV) lamps mounted at various locations within an internal cabin of the vehicle, wherein the UV lamps are configured to receive electrical power from the power bus and emit UV light into the internal cabin.

7. The power management system of claim 6, wherein the sanitizing system further includes a control unit including one or more processors, and, responsive to receiving the reduction command message, the control unit is configured to reduce an amount of power supplied to one or more of the UV lamps without causing the one or more UV lamps to cease emitting UV light.

8. The power management system of claim 7, wherein the control unit of the sanitizing system is configured to reduce the amount of power supplied to a first subset of the UV lamps prior to or instead of reducing the power supplied to a different, second subset of the UV lamps based on the first subset having a lower priority ranking than the second subset.

9. The power management system of claim 6, wherein the UV lamps are configured to emit the UV light at a designated wavelength or narrow wavelength range that is safe for human tissue.

10. The power management system of claim 9, wherein the designated wavelength is 222 nm.

11. The power management system of claim 1, further comprising a sensor operatively connected to the controller and configured to measure one or more characteristics of the electrical power on the power bus, the controller configured to monitor the electrical power on the power bus based on sensor signals from the sensor.

12. The power management system of claim 1, wherein the vehicle is an aircraft.

13. A method comprising:
monitoring, via a controller including one or more processors, electrical power on a power bus of a vehicle, the power bus electrically connecting a power source to multiple subsystems of the vehicle for powering the subsystems via the electrical power on the power bus;
responsive to determining that the electrical power on the power bus exceeds a designated power generation limit, generating a reduction command message for communication to a lowest-priority subsystem of the subsystems, the reduction command message instructing the lowest-priority subsystem to reduce power consumption; and
again monitoring the electrical power on the power bus after generating the reduction command message for communication to the lowest-priority subsystem, and, responsive to determining that the electrical power on the power bus still exceeds the designated power generation limit, generating a second reduction command message for communication to a next lowest-priority sub system of the subsystems.

14. The method of claim 13, further comprising determining a deficit between the electrical power on the power bus and the designated power generation limit, wherein the reduction command message is generated to include the deficit.

15. The method of claim 13, further comprising accessing a ranking of the subsystems in a memory device to determine the lowest-priority subsystem.

16. The method of claim 13, wherein the lowest-priority subsystem is a sanitizing system that includes a plurality of ultraviolet (UV) lamps mounted at various locations within an internal cabin of the vehicle and configured to emit UV light into the internal cabin using the electrical power on the power bus, wherein the method further comprises reducing an amount of power supplied to one or more of the UV lamps, based on the reduction command message, without causing the one or more UV lamps to cease emitting UV light.

17. The method of claim 16, further comprising controlling the UV lamps to emit the UV light at a designated wavelength or narrow wavelength range that is safe for human tissue at prolonged exposure.

18. A power management system comprising:
a controller including one or more processors, the controller configured to monitor electrical power on a power bus of a vehicle, the power bus electrically connecting a power source to multiple subsystems of the vehicle for powering the subsystems via the electrical power on the power bus; and
a sanitizing system that represents one of the subsystems, the sanitizing system including a plurality of ultraviolet (UV) lamps mounted at various locations within an internal cabin of the vehicle and configured to emit UV light into the internal cabin using the electrical power on the power bus,
the controller further configured to determine that the electrical power on the power bus exceeds a designated power generation limit, and, in response, generate a reduction command message for communication to the sanitizing system, the reduction command message instructing the sanitizing system to reduce power consumption,
the sanitizing system configured to reduce an amount of power supplied to one or more of the UV lamps, based on the reduction command message, to diminish the UV light output from the one or more UV lamps without causing the one or more UV lamps to cease emitting UV light.

19. A power management system comprising:
a controller including one or more processors, the controller configured to monitor electrical power on a power bus of a vehicle, the power bus electrically connecting a power source to multiple subsystems of the vehicle for powering the subsystems via the electrical power on the power bus,
the controller further configured to determine that the electrical power on the power bus exceeds a designated power generation limit, and, in response, generate a reduction command message for communication to a lowest-priority subsystem of the subsystems, the reduction command message instructing the lowest-priority subsystem to reduce power consumption,
wherein the lowest-priority subsystem is a sanitizing system that includes:
a plurality of ultraviolet (UV) lamps mounted at various locations within an internal cabin of the vehicle, wherein the UV lamps are configured to receive electrical power from the power bus and emit UV light into the internal cabin;
a control unit including one or more processors, and, responsive to receiving the reduction command message, the control unit is configured to reduce an amount of power supplied to one or more of the UV lamps without causing the one or more UV lamps to cease emitting UV light, and wherein the control unit is further configured to reduce the amount of power supplied to a first subset of the UV lamps prior to or instead of reducing the power supplied to a different, second subset of the UV lamps based on the first subset having a lower priority ranking than the second subset.

20. The power management system of claim 19, wherein the UV lamps are configured to emit the UV light at a designated wavelength or narrow wavelength range that is safe for human tissue.

* * * * *